United States Patent [19]
Miyaguchi

[11] 4,067,695
[45] Jan. 10, 1977

[54] GAS SENSING ELEMENT
[75] Inventor: Yōichiro Miyaguchi, Hachioji, Japan
[73] Assignee: Nittan Company, Limited, Japan
[21] Appl. No.: 760,529
[22] Filed: Jan. 19, 1977
[30] Foreign Application Priority Data
   Jan. 29, 1976  Japan ................................. 51-8784
   Apr. 12, 1976  Japan ................................ 51-40327
[51] Int. Cl.² ...................... G01N 27/12; G01N 31/06
[52] U.S. Cl. .................................... 23/254 E; 338/34
[58] Field of Search ................ 23/254 E; 338/34, 35; 73/23, 27 R

[56] References Cited
U.S. PATENT DOCUMENTS
3,255,324  6/1966  Ovshinsky ............................. 338/34
3,900,815  8/1975  Taguchi .............................. 23/254 E Primary Examiner—Robert M. Reese
Attorney, Agent, or Firm—Eugene E. Geoffrey, Jr.

[57] ABSTRACT

A gas sensing element which varies its resistivity upon the adsorption of gas and which has a sintered body including an oxyacid salt semiconductor and which may also contain carbon.

7 Claims, 9 Drawing Figures

GAS SENSING ELEMENT

This invention relates to a novel and improved gas sensing element of a type which adsorbs an ambient gas and varies its electrical resistivity.

Prior types of gas sensing elements have been known as metal oxide semiconductor gas sensing elements. However, such prior gas sensing elements may be affected by moisture and therefore operate erroneously, and moreover, they are relatively inferior in the selectivity of gases.

Accordingly, an object of this invention is to provide a novel and improved gas sensing element on which moisture will have little, if any, effect and which has superior gas selectivity.

According to this invention, the gas sensing element comprises a semiconductor body having a pair of electrodes and which changes its resistivity with changes in the concentration of gases in the ambient air and said semiconductor body consists of a sintered body of a composition including an oxyacid salt semiconductor.

The oxyacid salts which can be used in this invention are silicate, chromate, molybdate, tungstate and phosphate. Semiconductorized compositions of these oxyacid salts have not only gas sensing activity as in the case of known metal oxide semiconductor compositions, but also a gas selecting function based upon Lewis' acid effect. Moreover, moistureproofness of these novel compositions can be raised by a high degree of sintering treatment which could not be applied to prior metal oxide semiconductor compositions due to sensitivity deterioration.

The Lewis' acid effect is an interaction between a Lewis' base which serves to give an electron pair and a Lewis' acid which serves to receive the electron pair and is expressed, for example, as follows.

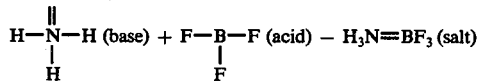

On the surface of an oxyacid salt semiconductor, there are fixed oxygen atoms or molecules, the number of which is limited by the ingredients of this semiconductor and which are balanced usually in accordance with its temperature and partial gas pressure. The adsorption reaction based upon the Lewis' effect takes place between these oxygen atoms or molecules and the ambient gases. As the semiconductors of this invention are mostly n-type, they receive electrons from the adsorbed gases. Thus, the number of electrons in the semiconductors increases and accordingly, the resistivity thereof decreases. When the adsorbed gas molecules are released, the original fixed oxygen condition is restored and the original resistivity is recovered.

The above reaction is governed by Arrhenius' equation of reaction velocity as follows.

$$k = A \exp(-Ea/RT)$$

where $k$ is the reaction velocity or reactivity, $A$ is the frequency factor, $Ea$ is the activation energy, $R$ is the gas constant and $T$ is the absolute temperature, and $A$ and $Ea$ are functions of temperature.

As the activation energies $Ea$ of the oxyacid salt semiconductors of this invention are highly affected by temperature as compared with the prior art metal oxide semiconductors, it is easy to select the gases by specifying the temperature of the element.

Now, the invention will be further described in conjunction with certain embodiments and with reference to the accompanying drawings.

Figure 1:
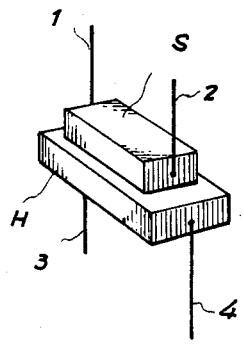
FIG. 1 is a perspective view of a gas sensing element according to this invention.

Referring to FIG. 1, showing an embodiment of this invention, the gas sensing element includes a sintered block S of oxyacid salt semiconductor composition having a pair of electrodes 1 and 2 and a heater element H having a pair of lead conductors 3 and 4. The sintered block S is bonded to the heater element H with a suitable heat-resistant adhesive such as glass frit. The heater element H serves the function of heating the block S at a predetermined fixed temperature and may preferably be a positive thermistor which changes its resistivity at this temperature.

As previously described, the oxyacid salt semiconductors which can be used in this invention are classified into five families. Now, the methods of manufacture of the gas sensing element of this invention with these semiconductors will be described hereinunder.

I. SILICATE COMPOUND SEMICONDUCTORS

This family of semiconductors includes $Fe_2SiO_4$, $ZrSiO_4$, $Be_2SiO_4$, $Mg_2SiO_4$, $Ni_2SiO_4$, $Ba_2SiO_4$, $Ca_2SiO_4$, $CaMgSiO_4$, $Cu_2Si_2O_7$, $Zn_2SiO_4$, and $Zn_2Si_2O_7$. In manufacture of these silicate compound semiconductors, stoichiometric amounts of silicon oxide and oxides or carbonates of the combining metal are mixed and fired at 1050°–1100° C. In this case, it is preferable to add oxides or carbonates of such metals as Sn, Nb, La and In, which serve as sintering suppressing agents and render the grain surface porous.

For example, in the case of $Zn_2SiO_4$, the materials are intermixed so as to fulfill a general formula:

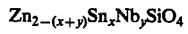

$$Zn_{2-(x+y)}Sn_xNb_ySiO_4$$

It has been found that the product becomes a semiconductor when $x = 0.2$ to $5.0$ mol% and $y = 0.05$ to $0.1$ mol%.

The fired product is then mixed with oxides of Pt, Pd, Rh, Ru or In as catalysts for improving gas selectivity and sensitivity, and pressed into a predetermined shape and sintered at 1250°–1350° C. As the catalysts in case of $Zn_2SiO_4$ semiconductor, a minute amount of palladium oxide may be added for improving the sensitivity to hydrogen and rhodium oxide or ruthenium oxide may be added for improving the sensitivity to propane. During this sintering step, valence control and production of non-stoichiometric composition and lattice defects are intentionally carried out in accordance with known techniques.

Figure 2:
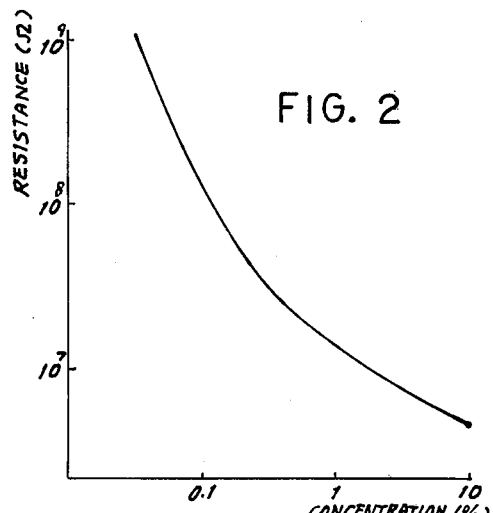
FIGS. 2 through 5 are characteristic diagrams which aid in the explanation of the features of preferred embodiments of this invention.

FIG. 2 shows a variation of the electrical resistance of a gas sensing element as shown in FIG. 1 with respect to a hydrogen concentration in the ambient air. This element was made of the abovementioned $Zn_2SiO_4$ semiconductor and kept at a specific temperature by the accompanying heater element.

Figure 3:
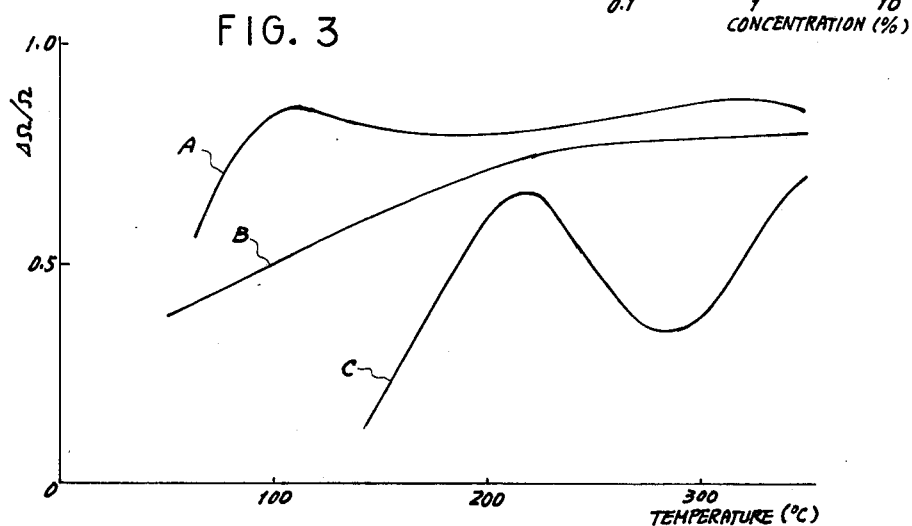

FIG. 3 shows a rate of resistance change of this gas sensing element with respect to the element temperature at a gas concentration of 1 percent, and curves A, B and C correspond respectively to hydrogen, carbon monoxide and n-butane. This teaches that the element is especially sensitive to hydrogen at about 100° C and especially insensitive to butane at about 300° C and, in other words, that specific gas selectivity can be imparted to this gas sensing element by keeping the element at a specific temperature.

II. CHROMATE COMPOUND SEMICONDUCTORS

This family of semiconductors includes $BaCrO_4$, $K_2CrO_4$, $PbCrO_4$ and $Sr_3(CrO_4)_2$. The method of manufacture of these semiconductors is quite similar to that of silicate compound semiconductors except for the use of chromium oxide in place of silicon oxide.

III. MOLYBDATE COMPOUND SEMICONDUCTORS

This family of semiconductors includes $Li_2MoO_4$, $La_2MoO_4$, $Na_2Mo_2O_7$, $CaMoO_4$, $PbMoO_4$, $Ba_2CaMoO_6$ and $Ca_2MgMoO_6$. In manufacture of these molybdate compound semiconductors, stoichiometric amounts of molybdenum oxide and carbonate of combining alkali-earth metal are mixed and fired under the same condition as the silicates. The fired product is mixed with an oxide or oxides of Pd, Pt, Ag, Ru and Rh as catalysts, if necessary, and then pressed into shape and sintered at 1300°–1400° C for 2–13 hours. In accordance with the same technique as in the silicate compound semiconductors, it is semiconductorized.

IV. TUNGSTATE COMPOUND SEMICONDUCTORS

This family of semiconductors includes $Li_2WO_4$, $Ba_2CaWO_6$, $Ba_2MgWO_6$, $BaSrMgWO_6$, $Ba_3WO_6$, $Sr_3WO_6$, $Ca_2MgWO_6$, $CaWO_4$, $MgWO_4$, $PbWO_4$, $FeWO_4$, $MnWO_4$, and $BaSrWO_6$. In manufacture, stoichiometric amounts of tungsten oxide ($WO_3$) and an oxide or carbonate of the combining metal are mixed and fired as in the case of silicates. After adding an oxide of Pt, Pd, Rh or In for improving gas selectivity as occasion demands, the fired product is pressed into shape and then sintered at 1300°–1400° C for 2–15 hours relying upon the combining metals. Then the same process as in the case of silicates follows for providing semiconductor gas sensing elements.

V. PHOSPHATE COMPOUND SEMICONDUCTORS

This family of semiconductors includes $Ba_{2.95}La_{0.05}(PO_4)_2$ and $Sr_{2.95}In_{0.05}(PO_4)_2$, for example. In the manufacture of these phosphate semiconductors, one or more of phosphates, Li(Fe, Mn) ($PO_4$), $NaMn(PO_4)$, $Sr_3(PO_4)_2$, $Ca_3(PO_4)_2$, $Ba_3(PO_4)_2$, $YPO_4$, $CePO_4$, $LaPO_4$, $ThPO_4$, $AlPO_4$, $InPO_4$, $TlPO_4$, $Fe_3(PO_4)_2$, $Ag_3PO_4$, $AgPO_3$, $GaPO_4$, $RbPO_3$, $ScPO_4$ and $BPO_4$, and of pyrophosphates, $ZrP_2O_7$, $SiP_2O_7$, $TiP_2O_7$, $HfP_2O_7$, $SnP_2O_7$ and $UP_2O_7$, and an oxide of the combining metal are mixed and fired or dried. After adding a catalyst similar to the above as occasion demands, the product is shaped and sintered. During the sintering step, semiconductorizing treatments are carried out as usual.

For instance, a suitable amount of indium phosphate $InPO_4$ or thallium phosphate $TlPO_4$ is added to strontium phosphate $Sr_3(PO_4)_2$ and, as occasion demands, one or more of phosphates and oxides of Pt, Pd, Rh, Ru, Ag, Au and Zr is added as a catalyst for improving sensitivity. The mixture is ground by a ball-mill and dried into powder. This powder is then pressed into shape and sintered in an electric furnace at about 1200° C to obtain phosphate anhydride semiconductor.

Although the gas sensing elements made of sintered oxyacid semiconductors as above exhibit high moisture-proofness as described later, they have a high resistance such as $10^7$ to $10^{10}$ ohms as shown in FIG. 2 so that their detection circuits may become undesirably complicated and costly. According to the second feature of this invention, however, the resistance of the element can be materially reduced by adding carbon in the semiconductor composition.

EXAMPLE

Powdered active charcoal having a particle size of 400–500 mesh (Tyler's standard sieve) is washed with alcohol and water and dried enough at 120° C. Then, it is rinsed in a solution of one or more metal salts, such as salts of Pd, Rh, Ru, Au, Ni, Co, Cr, Mn and Ag, which have a gas sensing catalyst effect. In order to obtain efficient deposition of the metal salts, the solution may be gelatinated by pH control, if necessary. After washed with water and dried, it is rinsed in a dilute phosphate solution, as occasion demands, for the purpose of improving refractoriness and semiconductor affinity of the carbon particles. The charcoal is preferably as hard as possible, in order to obtain stable conductivity and uniform elements.

$Zn_2SiO_4$ having high resistivity such as $10^{16}$ ohms or above is mixed with 0.05–0.1 mol% each of $La_2O_3$ and $TiO_2$ and 0.1–0.2 mol% of $SnO_2$ and then sintered at 1100°–1300° C for 2 hours and semiconductorized. This zinc silicate semiconductor, which has resistivity of $10^5$ to $10^7$ ohms, is pulverized below 300 mesh and then intermixed with the above prepared carbon particles by a ball-mill. The mixing ratio of carbon to zinc silicate is preferably 1/10 to ½ by weight. This powdered mixture is shaped and sintered at 600°–1000° C for 2–3 hours.

Figure 4:
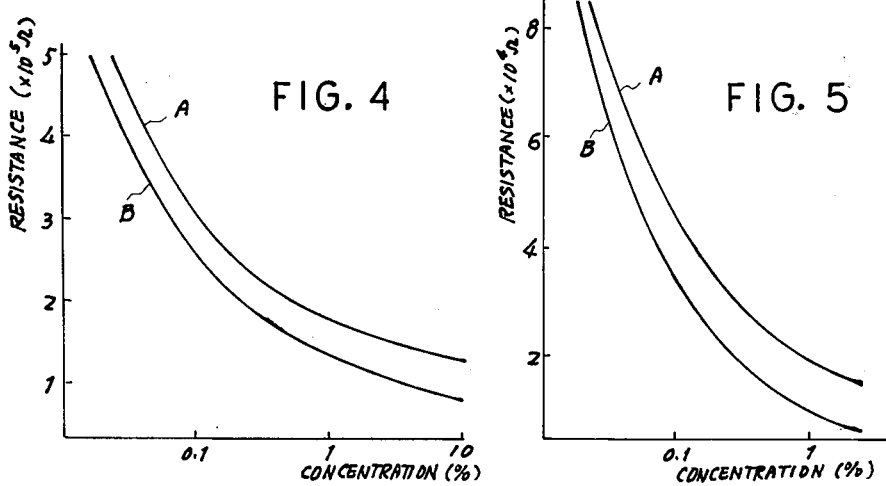
Figure 5:
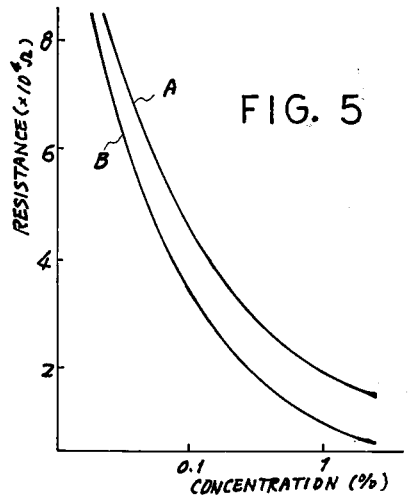

A gas sensing element made in accordance with the above example exhibited resistivity variations with gas concentration as shown in FIGS. 4 and 5. FIG. 4 was obtained with the element at room temperature in a butane containing atmosphere, while FIG. 5 was obtained with the same element heated at 80° C in a hydrogen containing atmosphere. In both drawings, curves A and B are obtained respectively at 30 and 60% humidities. As clearly understood from both figures, this carbon containing element exhibits relatively low resistivity in the order of $10^5$ ohms at room temperature, and therefore, can sense even butane to which the element is relatively insensitive, even at room temperature. Moreover, the sensitivity of this element is much improved by heating the element slightly. The curves A and B show the moistureproofness of the element of this invention.

Similar results were obtained by using charcoal and coke in place of active charcoal.

In order to reconfirm the improvement in this invention, comparative tests were carried out on the zinc silicate semiconductor element according to this invention and a commercially available metal oxide semiconductor element, and the results are given in FIGS. 6 through 9.

Figure 6:
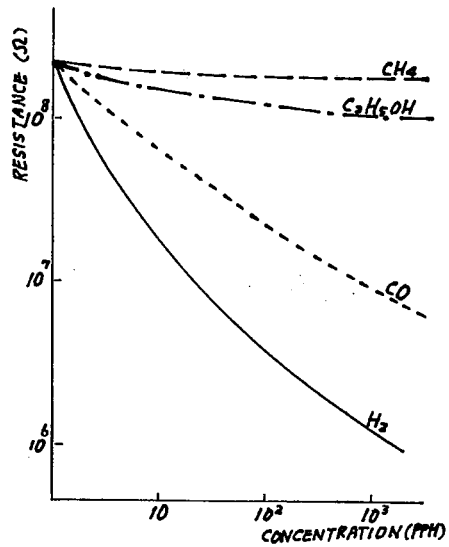
FIGS. 6 through 9 are characteristic diagrams which aid in the explanation of the superiority of this invention as compared with the prior art element.
Figure 7:
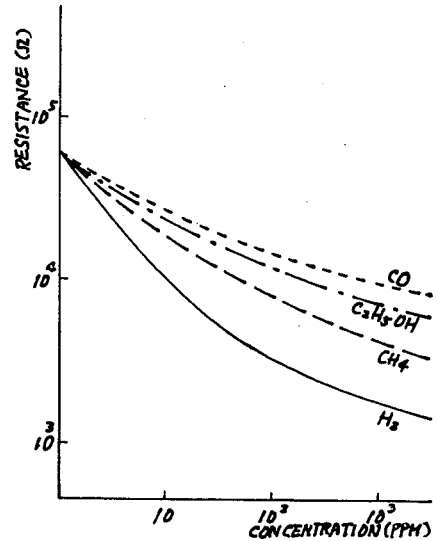

FIG. 6 shows the sensitivities of the inventive element to four gases, $H_2$, CO, $C_2H_5OH$ and $CH_4$, and FIG. 7 shows the sensitivities of the prior art element to the same gases. As shown, in the inventive element, the sensitivity is very low to organic gases such as methane and alcochol but is very high to inorganic gases such as hydrogen and carbon monoxide. However, in the prior art element, the difference in sensitivity is very small. More particularly, the inventive element has a special gas selecting property.

Figure 8:
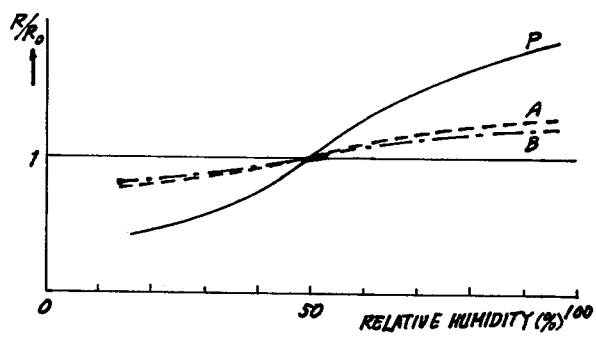
Figure 9:
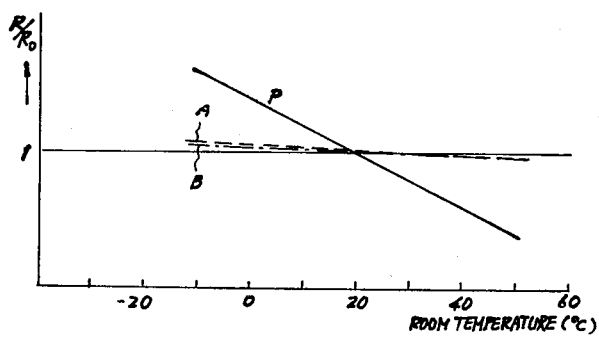

Although the sensitivity, that is, the concentration rate of change of resistivity, of the inventive element to hydrogen is higher than that of the prior art element as abovementioned, it is less affected by ambient conditions. FIGS. 8 and 9 show the resistivities of both inventive and prior art elements, which are expressed by the ratio of resistance R to the initial resistance $R_O$, at a specific concentration of hydrogen, varying with relative humidity and temperature of the ambient atmosphere, respectively. The ambient temperature is kept at 40° C in FIG. 8 and the humidity is kept at 50% in FIG. 9. In both figures, curve P corresponds to the prior art element and curves A and B correspond to the inventive element. Also, curve A corresponds to the element kept at 160° C and curve B corresponds to that at 120° C.

As clearly understood from both figures, the gas sensing element of this invention is less affected by ambient conditions than the prior art element.

What is claimed is:

1. A gas sensing element comprising a semiconductor body having a pair of electrodes and changing its electric resistivity with ambient gas concentration, wherein said semiconductor body consists of a sintered body of a composition containing an oxyacid salt compound semiconductor material.

2. A gas sensing element, according to claim 1 wherein said oxyacid salt is one selected from the group consisting of silicates, chromates, molybdates, tungstates and phosphates.

3. A gas sensing element according to claim 1 wherein said oxyacid salt compound semiconductor contains at least one element selected from the group consisting of Sn, Nb, La, and In.

4. A gas sensing element according to claim 1 wherein said composition contains at least one element selected from the group consisting of Pt, Pd, Rh, Ru, Au, Ag, Zr, In, Ni, Co, Cr, and Mn.

5. A gas sensing element according to claim 1 wherein said composition contains carbon.

6. A gas sensing element according to claim 1 wherein said semiconductor body is provided with a heating element.

7. A gas sensing element according to claim 1 wherein said heating element is a positive temperature coefficient resistor.

* * * * *

UNITED STATES PATENT OFFICE
CERTIFICATE OF CORRECTION

Patent No. 4,067,695         Dated January 10, 1978

Inventor(s) Yoichiro Miyaguchi

It is certified that error appears in the above-identified patent and that said Letters Patent are hereby corrected as shown below:

On the cover sheet, item [45] "January 10, 1977" should read

--January 10, 1978--.

Signed and Sealed this

Second Day of May 1978

[SEAL]

Attest:

RUTH C. MASON
Attesting Officer

LUTRELLE F. PARKER
Acting Commissioner of Patents and Trademarks